I

(12) United States Patent
Ray et al.

(10) Patent No.: US 7,504,255 B2
(45) Date of Patent: Mar. 17, 2009

(54) COMPOSITIONS AND METHODS FOR GENERATION OF INFECTIOUS HEPATITIS C VIRUS IN IMMORTALIZED HUMAN HEPATOCYTES

(75) Inventors: Ratna Ray, Saint Louis, MO (US); Ranjit Ray, Saint Louis, MO (US); Arnab Basu, Newton Lower Falls, MA (US); Tatsuo Kanda, Chiba (JP)

(73) Assignee: Saint Louis University, Saint Louis, MO (US)

( * ) Notice: Subject to any disclaimer, the term of this patent is extended or adjusted under 35 U.S.C. 154(b) by 0 days.

(21) Appl. No.: 11/506,161

(22) Filed: Aug. 17, 2006

(65) Prior Publication Data

US 2008/0081044 A1  Apr. 3, 2008

(51) Int. Cl.
  *C12N 5/00* (2006.01)
  *C12N 5/02* (2006.01)
  *A01N 63/00* (2006.01)
  *A61K 39/00* (2006.01)
  *A61K 39/12* (2006.01)
  *A61K 39/29* (2006.01)
  *A61K 39/275* (2006.01)

(52) U.S. Cl. ............... 435/346; 424/225.1; 424/204.1; 424/184.1; 424/93.6; 424/93.7; 435/325

(58) Field of Classification Search .................. None
See application file for complete search history.

(56) References Cited

U.S. PATENT DOCUMENTS

| | | | |
|---|---|---|---|
| 5,874,565 | A | 2/1999 | Rice et al. |
| 6,127,116 | A | 10/2000 | Rice et al. |
| 6,297,003 | B1 | 10/2001 | Rice et al. |
| 6,392,028 | B1 | 5/2002 | Rice, III et al. |
| 6,943,246 | B2 | 9/2005 | Rice et al. |
| 7,049,428 | B1 | 5/2006 | Rice, III et al. |
| 7,232,893 | B2 * | 6/2007 | Ray et al. ............ 530/416 |
| 2003/0017586 | A1 | 1/2003 | Rice et al. |
| 2003/0027130 | A1 | 2/2003 | Rice et al. |
| 2003/0028010 | A1 | 2/2003 | Rice et al. |
| 2003/0054341 | A1 | 3/2003 | Rice et al. |
| 2003/0073080 | A1 | 4/2003 | Rice et al. |
| 2006/0019245 | A1 | 1/2006 | Rice et al. |
| 2006/0099595 | A1 | 5/2006 | Rice et al. |
| 2006/0210969 | A1 | 9/2006 | Rice et al. |

OTHER PUBLICATIONS

Triyatni et al., Interaction of Hepatitis C Virus-Like Particles and Cells: a Model System for Studying Viral Binding and Entry, 2002, Journal of Virology, vol. 76, No. 18, pp. 9335-9344.*
Smith et al., Differential UGT1A1 Induction by Chrysin in Primary Human Hepatocytes and HepG2 Cells, 2005, The Journal of Pharmacology and Experimental Therapeutics, vol. 315, No. 3, pp. 1256-1264.*
Yanagi, Masayuki et al. Transcripts from a single full-length cDNA clone of hepatitis C virus are infectious when directly . . . , Proc. Natl. Ac vol. 94, Aug. 1997, 8738-8743.
Kolykhalov, Alexander et al., Hepatitis C Virus-Encoded Enzymatic Activities and Conserved RNA Elements in the . . . Journal of Virology, Feb. 2000, p. 2046-2051 vol. 74, No. 4.
Ray, Ranjit, et al. Hepatitis C virus core protein promotes immortalization of primary human hepatocytes. Virology. May 25, 2000;271(1):197-204.
Basu, Arnab et al., Hepatitis C virus core protein is necessary for the maintenance of immortalized human hepatocytes. Virology 2002, 298:53-62.
Kanda et al., Generation of Infectious Hepatitis C Virus in Immortalized Human Hepatocytes.J Virol. May 2006; 80(9): 4633-4639.
Minkyung et al., Production of infectious genotype 1a hepatitis C virus (Hutchinson strain) in cultured human hepatoma cells. PNAS, 2006, vol. 103, No. 7, 2310-2315.
Hong et al., Generation of Transmissible Hepatitis C Virions from a Molecular Clone in Chimpanzees, Virology, Mar. 1999, vol. 256, Issue 1, 30, pp. 36-44.
Han and Houghton, Group specific sequences and conserved secondary structures at the 3' end of HCV genome . . . Nucleic Acids Research, 1992, vol. 20, No. 13, 3520.
Lindenbach et al. Cell culture-grown hepatitis C virus is infectious in vivo and can be recultured in vitro. PNAS Mar. 7, 2006;103(10):3805-9. Epub Feb. 16, 2006.
Lindenbach et al., Complete replication of hepatitis C virus in cell culture.Science. Jul. 22, 2005;309(5734):623-6. Epub Jun. 9, 2005.
Basa, et al.; Hepatitis C virus core protein modulates the interferon-induced transacting factors of JAK/Stat signaling pathway but does not affect the activation of IRF-1 or 561 genes. Virology (2001) 288:379-390.
Blight et al.; Efficient replication of hepatitis C virus genotype 1a RNAs in cell culture. J. Virol. (2003) 77:3181-3190.
Cai, et al. Robust production of infectious hepatitis C virus (HCV) from stably HCV cDNA-transfected human hepatoma cells. J. Virol. (2005) 79:13963-13973.
Heller, et al., An in vitro model of hepatitis C virion production. Proc. Natl. Acad. Sci. USA (2005) 102:2579-2583.
Ikeda et al., Selectable subgenomic and genome length dicistronic RNAs derived from an infectious molecular clone of the HCV N strain of hepatitis C virus replicate efficiently in cultured Huh-7 cells. J. Virol. (2002) 76:2997 3006.
Kato et al., Sequence analysis of hepatitis C virus isolated from a fulminant hepatitis patient. J. Med. Virol. (2001) 64:334-339.
Kolykhalov et al., Transmission of hepatitis C by intrahepatic inoculation with transcribed RNA. Science (1997) 277:570-574.
Lin et al., Hepatitis C virus expression suppresses interferon signaling by degrading STAT1. (2005) Gastroenterology (2005) 128:1034-1041.

(Continued)

*Primary Examiner*—Bruce Campell
*Assistant Examiner*—Benjamin P Blumel
(74) *Attorney, Agent, or Firm*—Randolph Bratton

(57) ABSTRACT

The present invention provides a cell line capable producing infectious hepatitis C virus 1a (HCV 1a) particles in culture. Disclosed are compositions and methods for an HCV 1a (clone H77) transfected immortal human hepatocyte (IHH) capable of generating infectious HCV 1a virus particles in culture. Also disclosed are methods of using the cell line, or HCV 1a virus particles derived from said cell line, to screen for potential therapeutic agents which interfere with HCV 1a virus propagation to treat hepatic disease.

7 Claims, 6 Drawing Sheets

OTHER PUBLICATIONS

Majumder et al, Hepatitis C virus NS5A protein impairs TNF-mediated hepatic apoptosis, but not by an anti-FAS antibody, in transgenic mice. Virology (2002) 294:94-105.

Melen et al., Expression of hepatitis C virus core protein inhibits interferon-induced nuclear import of STATs. J. Med. Virol. (2004) 73:536-547.

Meyer et. al., Coexpression of hepatitis C virus E1 and E2 chimeric envelope glycoproteins displays separable ligand sensitivity and increases pseudotype infectious titer. J. Virol. (2004) 78:12838-12847.

Pawlotskiy, J.M. Current and future concepts in hepatitis C therapy. Semin. Liver Dis. (2005) 25:72-83.

Pietschmann et al. Persistent and transient replication of full length hepatitis C virus genomes in cell culture. J. Virol. (2002) 76:4008 4021.

Ray et al., Hepatitis C virus core protein: intriguing properties and functional relevance. FEMS Microbiol Lett. (2001) 202:149-156.

Saito et al. Hepatitis C virus infection is associated with the development of hepatocellular carcinoma. Proc. Natl. Acad. Sci. USA (1990) 87:6547-6549.

Simmonds et al., Classification of hepatitis C virus into six major genotypes and a series of subtypes by phylogenetic analysis of the NS-5 region. J. Gen. Virol. (1993) 74:2391-2399.

Wakita et al., Production of infectious hepatitis C virus in tissue culture from a cloned viral genome. Nature Med. (2005) 11:791-796.

Zhong et al., Robust hepatitis C virus infectin in vitro. Proc. Natl. Acad. Sci. USA (2005) 102:9294-9299.

Yi et al., Production of infectious genotype 1a hepatitis C virus (Hutchinson strain) in cultured human hapatome cells. PNAS, vol. 103, No. 7, (2006) 2310-2315.

* cited by examiner

A

B

C

SEQUENCE LISTING

```
<160> NUMBER OF SEQ ID NOS: 3

<210> SEQ ID NO 1
<211> LENGTH: 9646
<212> TYPE: DNA
<213> ORGANISM: Hepatitis C virus
<220> FEATURE:
<221> NAME/KEY: 5'UTR
<222> LOCATION: (1)..(341)
<220> FEATURE:
<221> NAME/KEY: 3'UTR
```

-continued

<222> LOCATION: (9375)..(9646)

<400> SEQUENCE: 1

| | | | | | |
|---|---|---|---|---|---|
| gccagccccc | tgatggggc | gacactccac | catgaatcac | tccctgtga | ggaactactg | 60 |
| tcttcacgca | gaaagcgtct | agccatggcg | ttagtatgag | tgtcgtgcag | cctccaggac | 120 |
| ccccctccc | gggagagcca | tagtggtctg | cggaaccggt | gagtacaccg | gaattgccag | 180 |
| gacgaccggg | tcctttcttg | gataaacccg | ctcaatgcct | ggagatttgg | gcgtgcccc | 240 |
| gcaagactgc | tagccgagta | gtgttgggtc | gcgaaaggcc | ttgtggtact | gcctgatagg | 300 |
| gtgcttgcga | gtgccccggg | aggtctcgta | gaccgtgcac | catgagcacg | aatcctaaac | 360 |
| ctcaaagaaa | aaccaaacgt | aacaccaacc | gtcgcccaca | ggacgtcaag | ttcccgggtg | 420 |
| gcggtcagat | cgttggtgga | gtttacttgt | tgccgcgcag | gggccctaga | ttgggtgtgc | 480 |
| gcgcgacgag | gaagacttcc | gagcggtcgc | aacctcgagg | tagacgtcag | cctatcccca | 540 |
| aggcacgtcg | gcccgagggc | aggacctggg | ctcagcccgg | gtacccttgg | cccctctatg | 600 |
| gcaatgaggg | ttgcgggtgg | gcgggatggc | tcctgtctcc | ccgtggctct | cggcctagct | 660 |
| ggggccccac | agaccccgg | cgtaggtcgc | gcaatttggg | taaggtcatc | gatacccta | 720 |
| cgtgcggctt | cgccgacctc | atggggtaca | taccgctcgt | cggcgcccct | cttggaggcg | 780 |
| ctgccagggc | cctggcgcat | ggcgtccggg | ttctggaaga | cggcgtgaac | tatgcaacag | 840 |
| ggaaccttcc | tggttgctct | ttctctatct | tccttctggc | cctgctctct | tgcctgactg | 900 |
| tgcccgcttc | agcctaccaa | gtgcgcaatt | cctcggggct | ttaccatgtc | accaatgatt | 960 |
| gccctaactc | gagtattgtg | tacgaggcgg | ccgatgccat | cctgcacact | ccggggtgtg | 1020 |
| tcccttgcgt | tcgcgagggt | aacgcctcga | ggtgttgggt | ggcggtgacc | ccacggtgg | 1080 |
| ccaccaggga | cggcaaactc | cccacaacgc | agcttcgacg | tcatatcgat | ctgcttgtcg | 1140 |
| ggagcgccac | cctctgctcg | gccctctacg | tgggggacct | gtgcgggtct | gtcttcttg | 1200 |
| ttggtcaact | gtttaccttc | tctcccaggc | gccactggac | gacgcaagac | tgcaattgtt | 1260 |
| ctatctatcc | cggccatata | acgggtcatc | gcatggcatg | ggatatgatg | atgaactggt | 1320 |
| cccctacggc | agcgttggtg | gtagctcagc | tgctccggat | cccacaagcc | atcatggaca | 1380 |
| tgatcgctgg | tgctcactgg | ggagtcctgg | cgggcatagc | gtatttctcc | atggtgggga | 1440 |
| actgggcgaa | ggtcctggta | gtgctgctgc | tatttgccgg | cgtcgacgcg | gaaacccacg | 1500 |
| tcaccggggg | aagtgccggc | cgcaccacgg | ctgggcttgt | tggtctccctt | acaccaggcg | 1560 |
| ccaagcagaa | catccaactg | atcaacacca | acggcagttg | gcacatcaat | agcacggcct | 1620 |
| tgaactgcaa | tgaaagcctt | aacaccggct | ggttagcagg | gctcttctat | cagcacaaat | 1680 |
| tcaactcttc | aggctgtcct | gagaggttgg | ccagctgccg | acgccttacc | gattttgccc | 1740 |
| agggctgggg | tcctatcagt | tatgccaacg | gaagcggcct | cgacgaacgc | ccctactgct | 1800 |
| ggcactaccc | tccaagacct | tgtggcattg | tgcccgcaaa | gagcgtgtgt | ggcccggtat | 1860 |
| attgcttcac | tcccagcccc | gtggtggtgg | gaacgaccga | caggtcgggc | gcgcctacct | 1920 |
| acagctgggg | tgcaaatgat | acggatgtct | tcgtccttaa | caacaccagg | ccaccgctgg | 1980 |
| gcaattggtt | cggttgtacc | tggatgaact | caactggatt | caccaaagtg | tgcggagcgc | 2040 |
| ccccttgtgt | catcggaggg | gtgggcaaca | acaccttgct | ctgccccact | gattgtttcc | 2100 |
| gcaagcatcc | ggaagccaca | tactctcggt | gcggctccgg | tccctggatt | acacccaggt | 2160 |
| gcatggtcga | ctaccgtat | aggctttggc | actatccttg | taccatcaat | tacaccatat | 2220 |
| tcaaagtcag | gatgtacgtg | ggaggggtcg | agcacaggct | ggaagcggcc | tgcaactgga | 2280 |

-continued

```
cgcggggcga acgctgtgat ctggaagaca gggacaggtc cgagctcagc ccattgctgc      2340
tgtccaccac acagtggcag gtccttccgt gttctttcac gaccctgcca gccttgtcca      2400
ccggcctcat ccacctccac cagaacattg tggacgtgca gtacttgtac ggggtagggt      2460
caagcatcgc gtcctgggcc attaagtggg agtacgtcgt tctcctgttc ctcctgcttg      2520
cagacgcgcg cgtctgctcc tgcttgtgga tgatgttact catatcccaa gcggaggcgg      2580
ctttggagaa cctcgtaata ctcaatgcag catccctggc cgggacgcac ggtcttgtgt      2640
ccttcctcgt gttcttctgc tttgcgtggt atctgaaggg taggtgggtg cccggagcgg      2700
tctacgcctt ctacgggatg tggcctctcc tcctgctcct gctggcgttg cctcagcggg      2760
catacgcact ggacacggag gtggccgcgt cgtgtggcgg cgttgttctt gtcgggttaa      2820
tggcgctgac tctgtcgcca tattacaagc gctacatcag ctggtgcatg tggtggcttc      2880
agtattttct gaccagagta gaagcgcaac tgcacgtgtg ggttcccccc ctcaacgtcc      2940 gggggggggcg cgatgccgtc atcttactca tgtgtgttgt acacccgact ctggtatttg      3000
acatcaccaa actactcctg gccatcttcg gaccccttg gattcttcaa gccagtttgc      3060
ttaaagtccc ctacttcgtg cgcgttcaag gccttctccg gatctgcgcg ctagcgcgga      3120
agatagccgg aggtcattac gtgcaaatgg ccatcatcaa gttagggcg cttactggca      3180 cctatgtgta taaccatctc acccctcttc gagactgggc gcacaacggc ctgcgagatc      3240
tggccgtggc tgtggaacca gtcgtcttct cccgaatgga gaccaagctc atcacgtggg      3300
gggcagatac cgccgcgtgc ggtgacatca tcaacggctt gccgtctct gcccgtaggg      3360 gccaggagat actgcttggg ccagccgacg gaatggtctc caaggggtgg aggttgctgg      3420
cgcccatcac ggcgtacgcc cagcagacga gaggcctcct agggtgtata atcaccagcc      3480
tgactggccg ggacaaaaac caagtggagg gtgaggtcca gatcgtgtca actgctaccc      3540
aaaccttcct ggcaacgtgc atcaatgggg tatgctggac tgtctaccac ggggccggaa      3600
cgaggaccat cgcatcaccc aagggtcctg tcatccagat gtataccaat gtggaccaag      3660
accttgtggg ctggcccgct cctcaaggtt cccgctcatt gacaccctgc acctgcggct      3720
cctcggacct ttacctggtc acgaggcacg ccgatgtcat tcccgtgcgc cggcgaggtg      3780
atagcagggg tagcctgctt tcgccccggc ccatttccta cttgaaaggc ctcctcgggg      3840
gtccgctgtt gtgccccgcg ggacacgccg tgggcctatt cagggccgcg gtgtgcaccc      3900
gtggagtggc taaggcggtg gactttatcc ctgtggagaa cctagagaca accatgagat      3960 cccccggtgtt cacggacaac tcctctccac cagcagtgcc ccagagcttc caggtggccc      4020
acctgcatgc tcccaccggc agcggtaaga gcaccaaggt cccggctgcg tacgcagccc      4080
agggctacaa ggtgttggtg ctcaacccct ctgttgctgc aacgctgggc tttggtgctt      4140
acatgtccaa ggcccatggg gttgatccta atatcaggac cggggtgaga acaattacca      4200
ctggcagccc catcacgtac tccacctacg gcaagttcct tgccgacggc gggtgctcag      4260
gaggtgctta tgacataata atttgtgacg agtgccactc cacggatgcc acatccatct      4320
tgggcatcgg cactgtcctt gaccaagcag agactgcggg ggcgagactg gttgtgctcg      4380
ccactgctac ccctcggggc tccgtcactg tgtcccatcc taacatcgag gaggttgctc      4440
tgtccaccac cggagagatc cctttttacg gcaaggctat ccccctcgag gtgatcaagg      4500
ggggaagaca tctcatcttc tgccactcaa agaagaagtg cgacgagctc gccgcgaagc      4560
tggtcgcatt gggcatcaat gccgtggcct actaccgcgg tcttgacgtg tctgtcatcc      4620
```

```
cgaccagcgg cgatgttgtc gtcgtgtcga ccgatgctct catgactggc tttaccggcg  4680
acttcgactc tgtgatagac tgcaacacgt gtgtcactca gacagtcgat ttcagccttg  4740
accctacctt taccattgag acaaccacgc tcccccagga tgctgtctcc aggactcaac  4800
gccggggcag gactggcagg gggaagccag gcatctacag atttgtggca ccgggggagc  4860
gcccctccgg catgttcgac tcgtccgtcc tctgtgagtg ctatgacgcg ggctgtgctt  4920
ggtatgagct cacgcccgcc gagactacag ttaggctacg agcgtacatg aacacccgg   4980
ggcttcccgt gtgccaggac catcttgaat tttgggaggg cgtctttacg ggcctcactc  5040
atatagatgc ccactttcta tcccagacaa agcagagtgg ggagaacttt ccttacctgg  5100
tagcgtacca agccaccgtg tgcgctaggg ctcaagcccc tcccccatcg tgggaccaga  5160
tgtggaagtg tttgatccgc cttaaaccca ccctccatgg gccaacaccc ctgctataca  5220
gactgggcgc tgttcagaat gaagtcaccc tgacgcaccc aatcaccaaa tacatcatga  5280
catgcatgtc ggccgacctg gaggtcgtca cgagcacctg ggtgctcgtt ggcggcgtcc  5340
tggctgctct ggccgcgtat tgcctgtcaa caggctgcgt ggtcatagtg ggcaggattg  5400
tcttgtccgg gaagccggca attataccttg acagggaggt tctctaccag gagttcgatg  5460
agatggaaga gtgctctcag cacttaccgt acatcgagca agggatgatg ctcgctgagc  5520
agttcaagca gaaggccctc ggcctcctgc agaccgcgtc cgccaagca gaggttatca   5580
cccctgctgt ccagaccaac tggcagaaac tcgaggtctt ctgggcgaag cacatgtgga  5640
atttcatcag tgggatacaa tacttggcgg gcctgtcaac gctgcctggt aaccccgcca  5700
ttgcttcatt gatggctttt acagctgccg tcaccagccc actaaccact ggccaaaccc  5760
tcctcttcaa catattgggg gggtgggtgg ctgcccagct cgccgccccc ggtgccgcta  5820
ccgcctttgt gggcgctggc ttagctggcg ccgccatcgg cagcgttgga ctggggaagg  5880
tcctcgtgga cattcttgca gggtatggcg cgggcgtggc gggagctctt gtagcattca  5940
agatcatgag cggtgaggtc ccctccacgg aggacctggt caatctgctg cccgccatcc  6000
tctcgcctgg agcccttgta gtcggtgtgg tctgcgcagc aatactgcgc cggcacgttg  6060
gcccgggcga gggggcagtg caatggatga accggctaat agccttcgcc tcccggggga  6120
accatgtttc ccccacgcac tacgtgccgg agagcgatgc agccgcccgc gtcactgcca  6180
tactcagcag cctcactgta acccagctcc tgaggcgact gcatcagtgg ataagctcgg  6240
agtgtaccac tccatgctcc ggttcctggc taagggacat ctgggactgg atatgcgagg  6300
tgctgagcga ctttaagacc tggctgaaag ccaagctcat gccacaactg cctgggattc  6360
cctttgtgtc ctgccagcgc gggtataggg gggtctggcg aggagacggc attatgcaca  6420
ctcgctgcca ctgtggagct gagatcactg gacatgtcaa aaacgggacg atgaggatcg  6480
tcggtcctag gacctgcagg aacatgtgga gtgggacgtt ccccattaac gcctacacca  6540
cgggcccctg tactccccct cctgcgccga ctataagtt cgcgctgtgg agggtgtctg   6600
cagaggaata cgtggagata aggcgggtgg gggacttcca ctacgtatcg ggtatgacta  6660
ctgacaatct taaatgcccg tgccagatcc catcgcccga ttttcaca gaattggacg    6720
gggtgcgcct acataggttt gcgccccctt gcaagccctt gctgcgggag gaggtatcat  6780
tcagagtagg actccacgag tacccggtgg ggtcgcaatt accttgcgag cccgaaccgg  6840
acgtagccgt gttgacgtcc atgctcactg atcccctcca tataacagca gaggcggccg  6900
ggagaaggtt ggcgagaggg tcaccccctt ctatggccag ctcctcggcc agccagctgt  6960
ccgctccatc tctcaaggca acttgcaccg ccaaccatga ctcccctgac gccgagctca  7020
```

```
tagaggctaa cctcctgtgg aggcaggaga tgggcggcaa catcaccagg gttgagtcag    7080
agaacaaagt ggtgattctg gactccttcg atccgcttgt ggcagaggag gatgagcggg    7140
aggtctccgt acccgcagaa attctgcgga agtctcggag attcgcccgg gccctgcccg    7200
tttgggcgcg gccggactac aaccccccgc tagtagagac gtggaaaaag cctgactacg    7260
aaccacctgt ggtccatggc tgcccgctac cacctccacg gtccctcct gtgcctccgc    7320 ctcggaaaaa gcgtacggtg gtcctcaccg aatcaaccct atctactgcc ttggccgagc    7380
ttgccaccaa aagttttggc agctcctcaa cttccggcat tacgggcgac aatacgacaa    7440
catcctctga gcccgcccct tctggctgcc ccccgactc cgacgttgag tcctattctt    7500
ccatgccccc cctggagggg gagcctgggg atccggatct cagcgacggg tcatggtcga    7560
cggtcagtag tggggccgac acggaagatg tcgtgtgctg ctcaatgtct tattcctgga    7620
caggcgcact cgtcaccccg tgcgctgcgg aagaacaaaa actgcccatc aacgcactga    7680
gcaactcgtt gctacgccat cacaatctgg tgtattccac cacttcacgc agtgcttgcc    7740
aaaggcagaa gaaagtcaca tttgacgac tgcaagttct ggacagccat taccaggacg    7800
tgctcaagga ggtcaaagca gcggcgtcaa aagtgaaggc taacttgcta tccgtagagg    7860
aagcttgcag cctgacgccc ccacattcag ccaaatccaa gtttggctat ggggcaaaag    7920
acgtccgttg ccatgccaga aaggccgtag cccacatcaa ctccgtgtgg aaagaccttc    7980
tggaagacag tgtaacacca atagacacta ccatcatggc caagaacgag gttttctgcg    8040
ttcagcctga gaagggggt cgtaagccag ctcgtctcat cgtgttcccc gacctgggcg    8100
tgcgcgtgtg cgagaagatg gccctgtacg acgtggttag caagctcccc ctggccgtga    8160
tgggaagctc ctacgattc caatactcac caggacagcg ggttgaattc ctcgtgcaag    8220
cgtggaagtc caagaagacc ccgatggggt tctcgtatga tacccgctgt tttgactcca    8280
cagtcactga gagcgacatc cgtacggagg aggcaattta ccaatgttgt gacctggacc    8340
cccaagcccg cgtggccatc aagtccctca ctgagaggct ttatgttggg ggccctctta    8400
ccaattcaag gggggaaaac tgcggctacc gcaggtgccg cgcgagcggc gtactgacaa    8460
ctagctgtgg taacaccctc acttgctaca tcaaggcccg ggcagcctgt cgagccgcag    8520
ggctccagga ctgcaccatg ctcgtgtgtg gcgacgactt agtcgttatc tgtgaaagtg    8580
cgggggtcca ggaggacgcg gcgagcctga gagccttcac ggaggctatg accaggtact    8640
ccgccccccc cggggacccc ccacaaccag aatacgactt ggagcttata acatcatgct    8700
cctccaacgt gtcagtcgcc cacgacggcg ctggaaagag ggtctactac cttacccgtg    8760
accctacaac cccctcgcg agagccgcgt gggagacagc aagacacact ccagtcaatt    8820
cctggctagg caacataatc atgtttgccc ccacactgtg ggcgaggatg atactgatga    8880
cccatttctt tagcgtcctc atagccaggg atcagcttga acaggctctt aactgtgaga    8940
tctacggagc ctgctactcc atagaaccac tggatctacc tccaatcatt caaagactcc    9000
atggcctcag cgcatttttca ctccacagtt actctccagg tgaaatcaat agggtggccg    9060
catgcctcag aaaacttggg gtcccgccct tgcgagcttg gagacaccgg gcccggagcg    9120
tccgcgctag gcttctgtcc agaggaggca gggctgccat atgtggcaag tacctcttca    9180
actgggcagt aagaacaaag ctcaaactca ctccaatagc ggccgctggc cggctggact    9240
tgtccggttg gttcacggct ggctacagcg gggagacat ttatcacagc gtgtctcatg    9300
cccggccccg ctggttctgg ttttgcctac tcctgctcgc tgcaggggta ggcatctacc    9360
```

-continued

```
tcctccccaa ccgatgaagg ttggggtaaa cactccggcc tcttaggcca tttcctgttt   9420 ttttttttt ttttttttt ttttttttt ttttttttt tttttttct ttttttttt   9480 tttttcctt ttttttttt tttttttct ttccttcttt tttcctttct tttccttcct   9540
tctttaatgg tggctccatc ttagccctag tcacggctag ctgtgaaagg tccgtgagcc   9600
gcatgactgc agagagtgct gatactggcc tctctgcaga tcatgt                 9646

<210> SEQ ID NO 2
<211> LENGTH: 20
<212> TYPE: DNA
<213> ORGANISM: Hepatitis C virus

<400> SEQUENCE: 2
acccgctgaa ttcctggaga                                                20

<210> SEQ ID NO 3
<211> LENGTH: 20
<212> TYPE: DNA
<213> ORGANISM: Hepatitis C virus

<400> SEQUENCE: 3
cacggtcttc tagacctccc                                                20
```

COMPOSITIONS AND METHODS FOR GENERATION OF INFECTIOUS HEPATITIS C VIRUS IN IMMORTALIZED HUMAN HEPATOCYTES

GOVERNMENT SUPPORT CLAUSE

The work disclosed herein was supported by research grants AI45144 (R.B.R) and CA85486 (R.R) from the National Institutes of Health. The U.S. Government has certain rights in this invention.

BACKGROUND OF THE INVENTION

1. Field of the Invention

This invention relates generally to compositions and methods of propagating hepatitis C viral genomes and infectious particles. Specifically, the invention is directed to an immortalized human hepatic cell line comprising the hepatitis C viral 1a genome, (IHH/HCV 1a) which is capable of replicating the hepatitis C viral 1a (HCV 1a) genotype and producing fully infectious HCV 1a virus particles.

2. Description of the Related Art

According to the American Liver Foundation, over 300,000 Americans are hospitalized each year for cirrhosis of the liver. The primary causes of cirrhosis are alcohol abuse and chronic hepatitis C(HCV). To date, approximately 3.9 million Americans suffer from hepatitis C. The most important feature of HCV infection is the development of chronic hepatitis in a significant number of infected individuals and the potential for disease progression to cirrhosis and hepatocellular carcinoma (6, 7, 11, 27). At present, the only approved therapy for chronic HCV infection is interferon (IFN)-α with or without ribavirin (9, 21), but this therapy fails to clear HCV from a significant number of patients (22). A number of HCV genomes have been cloned, and sequence divergence indicates several genotypes as well as a series of subtypes for this virus (28). In the United States, HCV genotypes 1a and 1b are predominant in patients with chronic hepatitis C (31). Progress in the understanding HCV biology has been hampered due to the lack of an efficient cell culture system for virus growth. The establishment of self-replicating HCV full-length genomic replicons from genotypes 1a and 1b in human hepatoma (Huh-7) cells has provided an important tool for the study of HCV replication mechanisms (3, 10, 23). Although some groups have reported the generation of infectious virus from transfection of genomic RNA of HCV genotype 2a into Huh-7 (5, 15, 29, 32), the generation of infectious HCV genotype 1a has not been successful to date, and therefore a long felt need exists.

The inventors and others have previously shown that HCV core protein transcriptionally regulates a number of cellular genes (26). The inventors have also previously described the generation of immortalized human hepatocytes (IHH) by transfection of the HCV core genomic region from genotype 1a (2, 25). IHH exhibit a weak level of HCV core protein expression, albumin secretion, glucose phosphatase activity, and absence of smooth muscle actin. IHH also displayed focal cytoplasmic and membrane staining for carcinoembryonic antigen (CEA), biliary glycoprotein (BGP1/CEACAM1) and nonspecific cross-reacting antigen (NCA/CEACAM6), and expression of hepato-biliary transport marker genes (MRP, LST1 and NTCP). Together, these results suggested that IHH are well differentiated. HCV core protein selectively degrades STAT1, reduces phosphorylated STAT1 (P-STAT1) accumulation in the nucleus in a proteasome-dependent manner, and impairs IFN-α-induced signal transduction via suppressor of cytokine signaling-3 expression (1, 4, 16). HCV core protein is competent to partially rescue growth of a genetically engineered influenza A virus lacking its own IFN antagonist (4). The core protein can modulate interferon regulatory factor (IRF), Jak-STAT and inducible nitric oxide synthetase (iNOS) pathways, and suggest mechanisms by which core could affect HCV persistence and pathogenesis (20). Since HCV core protein transcriptionally regulates several cellular genes involved in cell growth, apoptosis and defense mechanism, the inventors hypothesize that IHH may set the stage for HCV genome replication and assembly.

The inventors have sought to address the long felt need of providing a cell line permissible for HCV 1a replication and generation of infections virus particles. A cell line with this capability will be invaluable to researchers not only by providing easy access to HCV 1a infectious virus particles, but to identify HCV mediators and their pathways. In addition, it will be invaluable as a tool to screen new therapeutic strategies or potential pharmacological agents which interfere with the propagation of HCV and resulting diseases caused by the virus.

SUMMARY OF THE INVENTION

Progress in the understanding hepatitis C virus (HCV) biology has remained challenging due to the lack of an efficient cell culture system for virus growth. Therefore, the inventors examined HCV core protein mediated immortalized human hepatocytes (IHH) for support of HCV 1a genomic replication, infectious particle generation, and propagation. In vitro transcribed HCV full-length RNA from genotype 1a (clone H77) was electroporated into IHH. Viral RNA replication was evident by reverse transcriptase-polymerase chain reaction (RT-PCR) analysis of cellular RNA isolated from the HCV 1a genome-transfected IHH (IHH/HCV 1a). HCV full-length genome transfected IHH also displayed viral protein expression as indicated by indirect immunofluorescence. In contrast, cells transfected with polymerase-defective HCV (H77/GND) RNA as a negative control did not exhibit expression of viral genome. Immunogold labeling and transmission electronic microscopy demonstrated localization of the viral E1 protein in the rough endoplasmic reticulum of RNA transfected IHH. Virus-like particles of ~50 nm in the cytoplasm were also observed. Naive IHH, inoculated with culture medium from HCV full-length genome transfected cells, displayed NS5a protein expression in a dilution dependent manner, which was reduced upon prior incubation of the inoculums with HCV infected patient serum. Based on NS5a positive immunofluorescence, the inventors determined ~$4.5\times10^4$–$1\times10^5$ fluorescent focus units (ffu)/ml of cell culture medium, removed from cultures of IHH transfected with H77 full-length RNA. A similar level of virus growth was observed by transfection of RNA from HCV genotype 2a (JFH1) into IHH. Taken together, our results suggest that IHH support HCV genome replication and virus assembly.

Therefore, an object of this invention is an immortal human hepatocyte comprising a full length HCV 1a genome (IHH/HCV 1a) capable of sustaining HCV 1a replication and generation of infectious HCV 1a virus particles.

In another embodiment, an object of this invention is an infectious HCV 1a virus particle produced by IHH/HCV 1a in culture.

In another embodiment, an object of this invention is a method of using IHH/HCV 1a to study HCV 1a biology and to screen for potential therapeutic agents which interfere with any stage of HCV propagation.

In another embodiment, IHH/HCV 1a derived HCV 1a virus particles may be used to study infectivity and screen therapeutic agents which may interfere with HCV 1a infection.

It is envisioned that the instant IHH/HCV 1a will be propagated in vitro, frozen for convenient storage, and typically manipulated as a conventional cell line.

It is also envisioned that IHH/HCV 1a, its prodigy, or derivatives, in whole or in part, maybe be used separately, or combined with other biological systems to screen for therapeutic agents which interfere with pathways of viral replication, assembly, and infection, for development of pharmaceutical compositions for the treatment of hepatic disease.

DETAILED DESCRIPTION OF THE INVENTION

Figure 1:
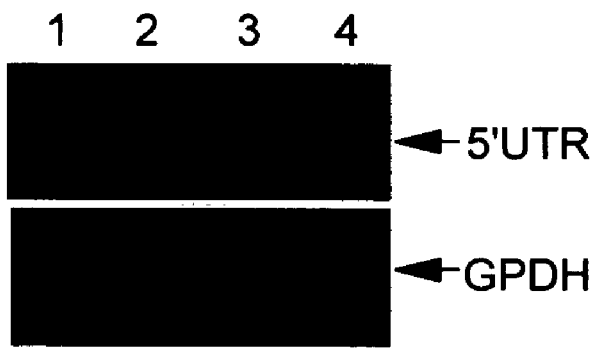
FIG. 1: HCV RNA and protein expression in IHH. Panel A: RT-PCR analysis was performed using 5' untranslated region (5' UTR) specific primers from RNA isolated at day 5 from two different sets of IHH transfected with H77/GND RNA as a negative control (lanes 1 and 2) and H77 RNA (lanes 3 and 4). GPDH was amplified as an internal control. The sizes of the amplified bands were verified from the migration of a φX174-HaeIII digested DNA marker (not shown). Panel B: Western blot analysis for core protein expression in H77/GND RNA transfected (lane 1), and H77 RNA transfected (lane 2) IHH, using a specific antiserum. The blot was re-probed with antibody to actin for similar protein load in each lane. Panel C: Western blot analysis for NS3 protein expression in two different sets of IHH transfected with H77/GND RNA (lanes 1 and 2) and H77 RNA (lanes 3 and 4), using a specific monoclonal antibody. The blot was re-probed with antibody to actin for similar protein load in each lane. The molecular weight of the protein bands were verified from the migration of protein molecular weight markers (Cambrex, Rockland, Me.).
Figure 1:
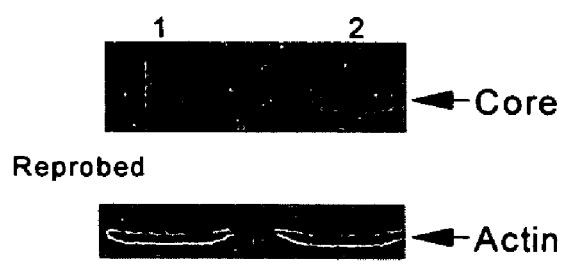
Figure 1:
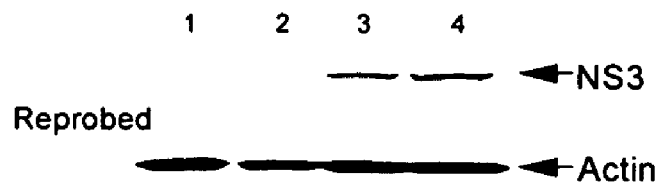

HCV replication is believed to proceed as follows. HCV RNA is translated directly to a precursor viral polypeptide. This precursor polypeptide is then proteolytically cleaved to form individual proteins. A replicase complex amplifies viral RNA genome via a minus strand intermediate. Plus strand RNA progeny are then packaged into virus particles which acquire their envelope by budding into the lumen of the endoplasmic reticulum. HCV particles are exported via the constitutive secretory pathway. Based on this working principle, the inventors have shown that IHH support HCV genome replication and protein expression from genotype 1a.

Transmission electron microscopy and immunogold labeling, using a monoclonal antibody directed against HCV E1 glycoprotein, demonstrated the localization of this antigen to the rough endoplasmic reticulum, and also the formation of virus-like particles. The inventors transferred culture medium, previously in contact with IHH/HCV 1a, to naive IHH cultures and subsequently detected HCV infection in these cells by RT-PCR and indirect immunofluorescence.

The inventors observed JFH1 replication and virus assembly in IHH. The infectious unit of JFH1 replicated in IHH similarly to JFH1 grown in Huh-7 cells or its derivatives. The inventors also observed similar levels of genomic copy of H77 or JFH1, in transfected IHH culture supernatant, and in fluorescence focus units. The inventors did not purify virus particles for negative staining due to the relatively low infectious units present in the culture medium.

Three different groups of investigators have reported different densities of HCV 2a particles. Zhong et al. (32) observed peak infectivity from an apparent density of 1.105 gm/ml, Wakita et al. (29) observed peak infectivity at a density of ~1.15 gm/ml, and Lidenbach et al. (15) observed a broad distribution of virus infectivity over a range of 1.01 to 1.12 gm/ml. A similar finding suggesting a variation of buoyant density of cell culture grown HCV 2a between 1.06 and 1.16 gm/ml was reported by Cai et al. (5). HCV is known to associate with serum immunoglobulin and lipoproteins (24). The inventors found HCV infectivity within a density range of 1.09 to 1.12 sucrose gradient, which did not correlate with the highest copy number of virus genomic RNA (data not shown).

Recently, HCV production was reported from a HCV-ribozyme construct of genotype 1a (clone H77) in Huh-7 cells, although infectivity of virus was not demonstrated (8). Virus genome replication and assembly are multi-step processes, and are influenced by the intracellular milieu. Inhibition of host cell growth and induction of cytokines, such as interferons, may have an impact on prevention of virus replication (3). The inventors provide evidence for HCV replication and assembly of infectious genotype 1a in IHH. Others have not been successful in generating infectious HCV 1a from cells in culture.

The inventors speculate that the cellular defense mechanism against HCV infection is attenuated or compromised in IHH. The inventors realize the importance of determining these factors including mechanisms for growth of HCV in IHH, as well as identification of critical control points in the HCV life-cycle. The inventors currently have studies in progress to determine cellular and viral factors influencing virus growth, such as serial passage requirements for adaptation in IHH, mutations at specific sites of the HCV genome, and selection of cell populations for attenuation protective mechanisms. The inventors realize the importance of further characterizing biophysical properties of cell culture grown HCV 1a, including infectivity in appropriate animal models.

Therefore, the invention is drawn to (1) an immortal human hepatocyte cell line comprising a full length HCV 1a genome, capable of producing infectious HCV 1a virus particles, (2) methods of producing said cell line (3) methods of producing infectious HCV 1a virus particles, (4) methods of using said cell line for evaluating potential therapeutic agents for the prevention of HCV 1a propagation, (5) methods of using cell culture derived HCV 1a for evaluating potential therapeutic agents for the prevention infection.

The term "HCV" refers to hepatitis type C virus.

The term "1a", or "HCV 1a" refers to the 1a genotype of the hepatitis C virus.

The term "immortalized human hepatocytes" or "IHH" means generally a cell line derived from human hepatocytes and modified to be maintained indefinitely in vitro. More specifically it refers to an IHH, made by the inventors and previously fully described by them (2, 25) which are herein incorporated by reference.

The term "H77" refers to full length HCV 1a genomic oligonucleotide, as provided by the H77 clone previously described in detail (3, 13, 14) which are herein incorporated by reference.

The term IHH/HCV 1a refers to the instance invention of an IHH cell comprising a full lengthen HCV 1a genome capable of producing HCV 1a infectious virus particles.

The term "propagation" in reference to HCV refers to the process in whole or in part of infection or transfection, oligonucleotide replication, protein synthesis, virus particle assemble, release and re-infection.

Sequence identity or percent identity is intended to mean the percentage of same residues between two sequences. The reference sequence is Hepatitis C Viral Genome 1a accession number NC_004102 which is derived from AF009606. In all of the sequence comparisons, the two sequences being compared are aligned using the Clustal method (Higgins et al, Cabios 8:189-191, 1992) of multiple sequence alignment in the Lasergene biocomputing software (DNASTAR, INC, Madison, Wis.). In this method, multiple alignments are carried out in a progressive manner, in which larger and larger alignment groups are assembled using similarity scores calculated from a series of pairwise alignments. Optimal sequence alignments are obtained by finding the maximum alignment score, which is the average of all scores between the separate residues in the alignment, determined from a residue weight table representing the probability of a given amino acid change occurring in two related proteins over a given evolutionary interval. Penalties for opening and lengthening gaps in the alignment contribute to the score. The default parameters used with this program are as follows: gap penalty for multiple alignment=10; gap length penalty for multiple alignment=10; k-tuple value in pairwise alignment=1; gap penalty in pairwise alignment=3; window value in pairwise alignment=5; diagonals saved in pairwise alignment=5. The residue weight table used for the alignment program is PAM250 (Dayhoff et al., in Atlas of Protein Sequence and Structure, Dayhoff, Ed., NBRF, Washington, Vol. 5, suppl. 3, p. 345, 1978).

Table 1 shows the calculations of identity for comparisons of HCV derived from H77.

TABLE 1

| Percent Identity of HCV H77 derived sequences | | |
|---|---|---|
| Species | Accession number | Percent Identity |
| Hepatitis C Viral Genome 1a (H77) | NC_004102 | 100 |
| Hepatitis C virus polyprotein gene, complete cds 1a | AF009606 | 100 |
| Hepatitis C virus strain H77 pCV-H11 | AF011752 | 99 |

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

EXAMPLE 1

Replication of HCV Genome and Virus Protein Expression

The object of the invention is a cell line to provide HCV 1a genotype replication and generation of infectious virus particles. The inventors have previously described the generation of immortalized human hepatocytes (IHH) by transfection of HCV core genomic region from genotype 1a, as well as the conditions and requirements for maintaining IHH in culture (2, 25) which are herein incorporated by reference. Full-length RNAs from HCV genotype 1a (clone H77, GenBank Accession number NC_004102, SEQ ID NO:1) has also previously described (3, 13, 14) and are herein incorporated by reference. Restriction enzyme Xba I and T7 RNA polymerase were obtained from Invitrogen and Promega, (Madison, Wis.) respectively and used according to the supplier's protocol. The individual elements of the inventors' methodology is generally well known and described in detail in numerous laboratory protocols, one of which is Molecular Cloning 2$^{nd}$ edition, (1989) Sambrook, J., Fritsch, E. F. and Maniatis, J., Cold Spring Harbor.

Clone H77 contains a 5' untranslated region (5' UTR) coding sequence and 3' UTR, which is suggested to be necessary for replication (14, 30). In vitro transcribed full-length HCV 1a RNA from clone H77 was used for transfection of IHH which was performed by electroporation. Polymerase defective H77/GND RNA was similarly used as a negative control. H77 cDNA was first linearized by digestion with Xba I, and the linearized product purified by agarose gel electrophoresis. Purified H77 cDNA was then transcribed in vitro using T7 RNA polymerase. In vitro transcribed RNA (1-2 μg) was introduced into 5×10$^6$ IHH by electroporation (950 μF and 270 V) using a BioRad Gene pulse Xcell system (Hercules, Calif.). The transfected cells were plated on collagen coated plastic dishes, and maintained using standard cell culture techniques to allow for HCV replication.

Total cellular RNA was extracted 5 days post transfection. For detection of HCV genome, total cellular RNA and random hexamer were used for cDNA synthesis with a SuperScript III first-strand synthesis system (Invitrogen), according to the supplier's protocol. PCR amplification was performed with cDNA as a template, using sense (5'-ACCCGCTGAATTCCTGGAGA-3') (SEQ ID NO:2) and antisense (5'-CACGGTCTTCTAGACCTCCC-3') (SEQ ID NO:3) primers from 5' UTR, at 94° C. for 30s, annealing at 55° C. for 60s, and extension at 72° C. for 90s. GPDH was used as an internal control, with specific primers (17). RT-PCR analyses suggested amplification of 120 bp sequence from the 5' UTR (FIG. 1, panel A). In contrast, cells transfected with H77/GND RNA did not exhibit the presence of HCV genomic sequence. To rule out the integration of H77 plasmid DNA into IHH, the genomic DNA from cell lines were isolated and examined for HCV genome by PCR. These results suggested the absence of HCV sequence, indicating HCV genomic RNA replication in the cytoplasm of IHH (data not shown). Filtered culture supernatant was also treated with RNaseA prior to isolation of viral RNA. RT-PCR was performed for NS5A region (17) and the inventors have observed amplification of specific RNA sequence.

Western blot analysis was performed to analyze the expression of core and NS3 proteins in control and experimental cells using specific antibodies. An equal amount of proteins from whole cell lysates in sample buffer were separated by SDS-PAGE. Proteins were transferred onto nitrocellulose, incubated with specific antibodies, and detected by chemiluminescence (Amersham, Piscataway, N.J.). HCV core protein was detected by a specific rabbit antiserum, and NS3 was detected by a specific mouse monoclonal antibody (Virogen, Watertown, Mass.). Blots were stripped and re-probed using a mouse monoclonal antibody to actin (Oncogene Science, Cambridge, Mass.). IHH supporting HCV genome replication displayed the presence of core (~21 kDa) and NS3 (~63 kDa) proteins (FIG. 1, panels B and C). On the other hand, IHH transfected with H77/GND RNA did not show a detectable level of core or NS3 proteins. A weak level of core protein was detected in this set of IHH for immortalization by HCV core protein (FIG. 1, panel B). IHH transfected with HCV full-length RNA were passaged at 4 or 5 day intervals. HCV RNA and protein expression were detected up to 12 days of cell culture, and discontinued for the lack of growth after 2 weeks.

Figure 2:
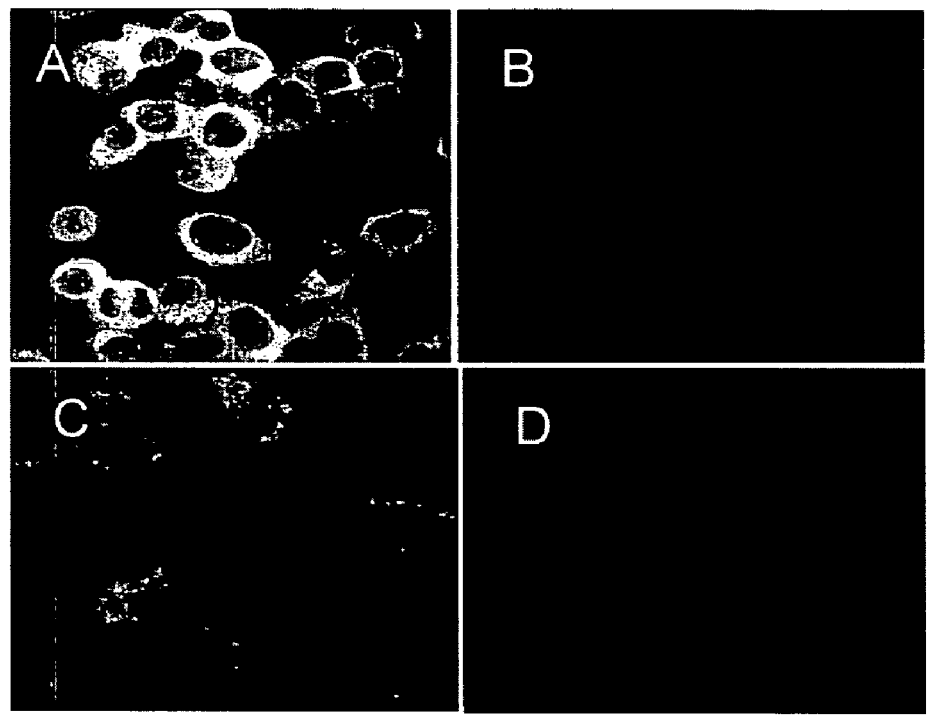
FIG. 2: Intracellular expression of HCV proteins. IHH transfected with RNA from H77 clone (panel A) or H77/GND RNA transfected negative control (panel B) were treated with NS5a specific monoclonal antibody for detection of protein expression by intracellular immunofluorescence after 5 days of transfection. IHH were similarly transfected with RNA from JFH1 clone (panel C) and JFH1/GND RNA transfected negative control (panel D) for intracellular localization of NS3 using a specific monoclonal antibody. Green color indicates NS5a staining and red color for NS3 staining.

To further examine intracellular expression of HCV protein, IHH transfected with H77 RNA were fixed with 3.7% formaldehyde and incubated at room temperature for 1 h with monoclonal antibodies to NS5a (Biogenesis, Kingstone, N.H.). Cells were washed three times with PBS and stained with anti-mouse Ig conjugated with Alexa 568 (Molecular Probes, Eugene, Oreg.), and mounted for fluorescence microscopy. Primary antibodies and secondary antibody-fluorochrome conjugates were titrated for use of optimum dilutions where there was no background fluorescence. The inventors have observed cytoplasmic expression of NS5a (FIG. 2, panel A) in 60% IHH after 5 days of transfection. HCV genotype 2a (clone JFH1) has been shown to grow in Huh-7 cells or its derivatives (5, 15, 29, 32). In vitro transcribed RNA from clone JFH1 was used for transfection of IHH to determine if the immortalized hepatocyte cell line supports HCV growth. Intracellular localization of NS3 protein from JFH1 RNA transfected IHH was detected by immunofluorescence (FIG. 2, panel C). The inventors have also used Huh-7.5 cells transfected with JFH1 RNA as a positive control (29) and observed NS3 expression by indirect immunofluorescence (data not shown). On the other hand, IHH similarly transfected with RNA from H77/GND or JFH1/GND clone did not display virus protein expression by immunofluorescence (FIG. 2, panels B and D).

EXAMPLE 2

Immunogold Localization of Virus-Like Particles

Figure 3:
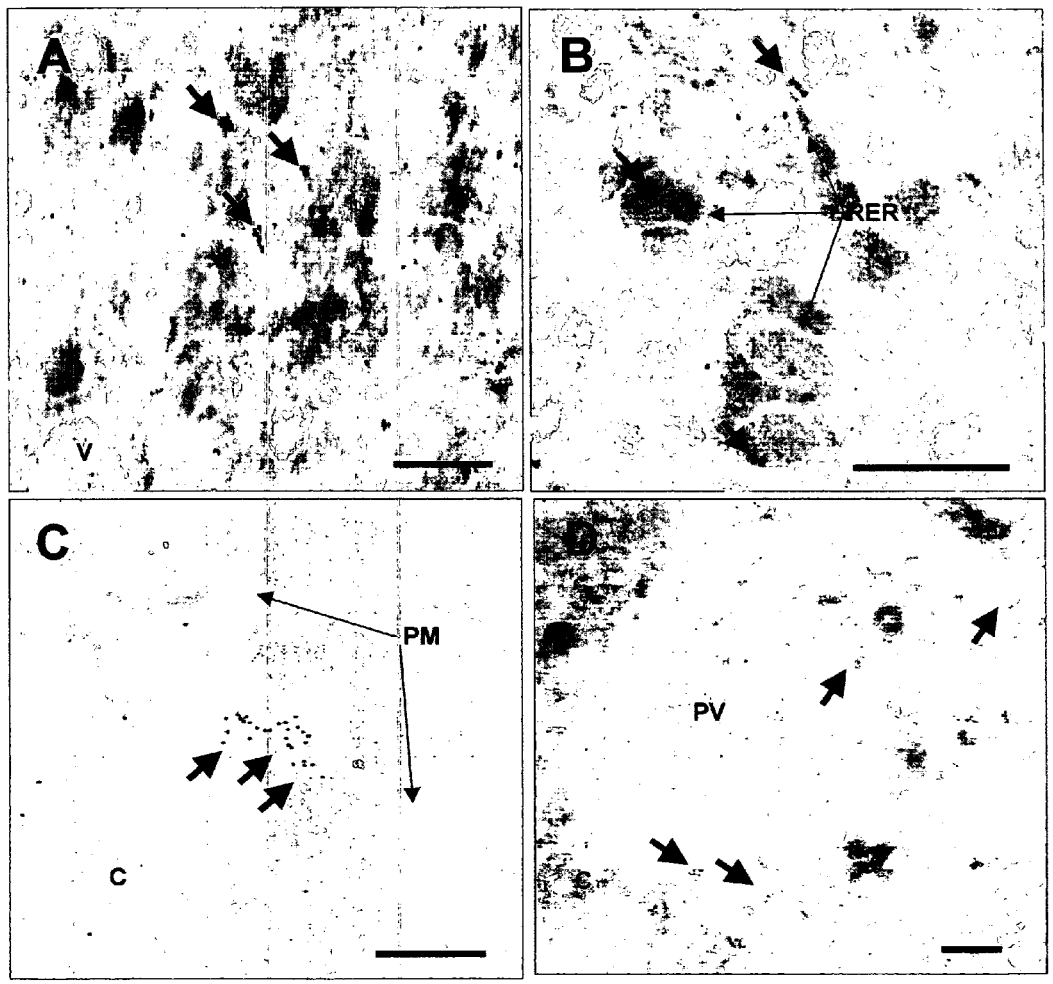
FIG. 3: Immunogold localization of HCV E1 protein and virus-like particles in IHH with a specific monoclonal antibody. Panel A: Localization of virus-like particles in the cytoplasm are indicated by arrows. Panel B: Localization of HCV E1 protein to the rough endoplasmic reticulum is marked by arrows. Panel C: Localization of virus-like particles in the cortical cytoplasm adjacent to the plasma membrane. Panel D: Localization of virus-like particles in a large phagic vacuole in the cytoplasm of IHH is shown by arrows. Panel E: Clusters of CG indicated by arrows show virus-like particles in IHH. The labeled particle indicated by an arrow and with an asterisk is shown at higher magnification in the inset. As observed by light microscopy, IHH contain cytoplasmic vacuoles and lipid droplets. Panel F: H77/GND RNA-transfected control section of IHH incubated with monoclonal antibody to E1 glycoprotein did not exhibit immunogold labeling. Other negative controls consisted of labeling with normal mouse IgG and omitting the primary antibody (not shown). The abbreviations used are: C—cytoplasm, M—mitochondrion, PM—plasma membrane, RER—rough endoplasmic reticulum, V—vacuole, LD—lipid droplet, PV—phagic vacuole. Magnification bars are 0.25 µm in panels A-F, and 0.1 µm in the inset in panel E.
Figure 3:
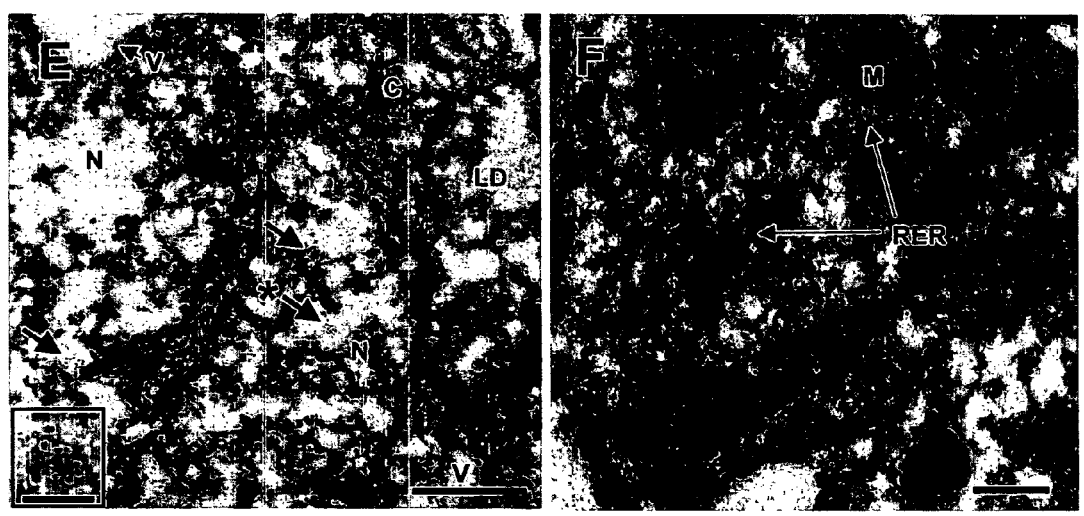

Phase contrast microscopy suggested that HCV genome transfected IHH were swollen with large vacuoles in the cytoplasm, whereas negative controls did not show any detectable changes. The inventors also examined cellular changes using an electron microscopy, and found at the ultrastructural level that some of these vacuoles appeared to be empty (FIG. 3, panels A and E). Others vacuoles contained lipid (FIG. 3, panel E) or material isolated for degradation (FIG. 3, panel D). Ultrastructural changes also included an increased polymorphism of nuclei (FIG. 3, panel E). Immunogold labeling was performed for localization of HCV like particles in transfected IHH. For this, transfected IHH (4 days in culture) were detached from collagen coated petridishes by a brief trypsin treatment, pelleted in a microcentrifuge, and fixed in 4% paraformaldehyde and 1% glutaraldehyde in PBS for 16 h at 4° C. After washing with PBS, cells were further washed in distilled water, dehydrated in ethanol, and infiltrated with L. R. White resin (London Resin Company, Berkshire, UK). The cell pellets were polymerized in BEEM capsules (Ted Pella, Inc., Redding, Calif.) at −20° C. under ultraviolet light. Thin sections were cut from blocks, collected on formvar-coated nickel grids, and blocked with 1% fish gelatin and 1% BSA in PBS for 10 min. Sections were incubated for 2 h in 1:100 dilution (titrated before hand for best results) of monoclonal antibody to E1 glycoprotein (305/C3) or normal mouse IgG in PBS containing 0.1% BSA, washed in PBS containing 0.1% BSA and incubated for 1 h in Protein A-10 nm colloidal gold (CG) diluted 1:200 in PBS containing 0.1% BSA. After washing with PBS, the grids were fixed for 3 min in glutaraldehyde, washed in distilled water, stained with uranyl acetate and lead citrate, and photographed with a JEOL 100 CX electron microscope. No clusters of CG particles were observed in controls which consisted of staining with normal mouse IgG, omitting the primary antibody, or staining mock-transfected IHH with the 305/C3 monoclonal antibody. Several hundred cells were evaluated in each case. Immunogold labeling with E1 specific monoclonal antibody demonstrated the presence of HCV-like particles and E1 protein in IHH. Numerous labeled virus-like particles were observed in the cytoplasm (FIG. 3, panels A and E) and near the plasma membrane (FIG. 3, panel C) of H77 RNA transfected IHH. The labeled particles were ~50 nm in diameter. Extensive labeling was also associated with the rough endoplasmic reticulum consistent with the synthesis of E1 viral protein (FIG. 3, panel B). In addition, the inventors observed cytoplasmic phagic vacuoles which contained gold-labeled virus-like particles (FIG. 3, panel D).

Processing of cells into LR White resin for immunogold localization omits the conventional osmium tetroxide fixation step to preserve antigenicity but comes at the cost of reduced tissue contrast. In addition, the identification of virus particles by immunogold labeling at the ultrastructural level can be problematic. For this, the inventors carried out a series of control experiments to insure labeling specificity. First, clusters of CG on virus-like particles, and single CG particles were observed in the endoplasmic reticulum in several independent anti-E1 labeling experiments. Second, H77/GND RNA transfected IHH (negative controls) showed no such clusters of CG in the cytoplasm or single CG particles localized along the endoplasmic reticulum or membranes (FIG. 3, panel F). Third, sections of HCV genome transfected IHH incubated with normal mouse IgG at similar IgG concentrations as used for the anti-E1 antibody did not result in any specific immunogold labeling. Fourth, omitting anti-E1 antibody did not result in any specific immunogold labeling. Finally, CG particles in the anti-E1 labeling experiments were primarily confined to cells and were not observed to any degree in the spaces around cells, again suggesting the labeling was specific for E1 protein in cells. Thus, the appearance of virus-like particles in RNA transfected IHH indicates that IHH support HCV 1a viral replication and assemble.

EXAMPLE 3

Infection of IHH by HCV from Culture Medium

Figure 4:
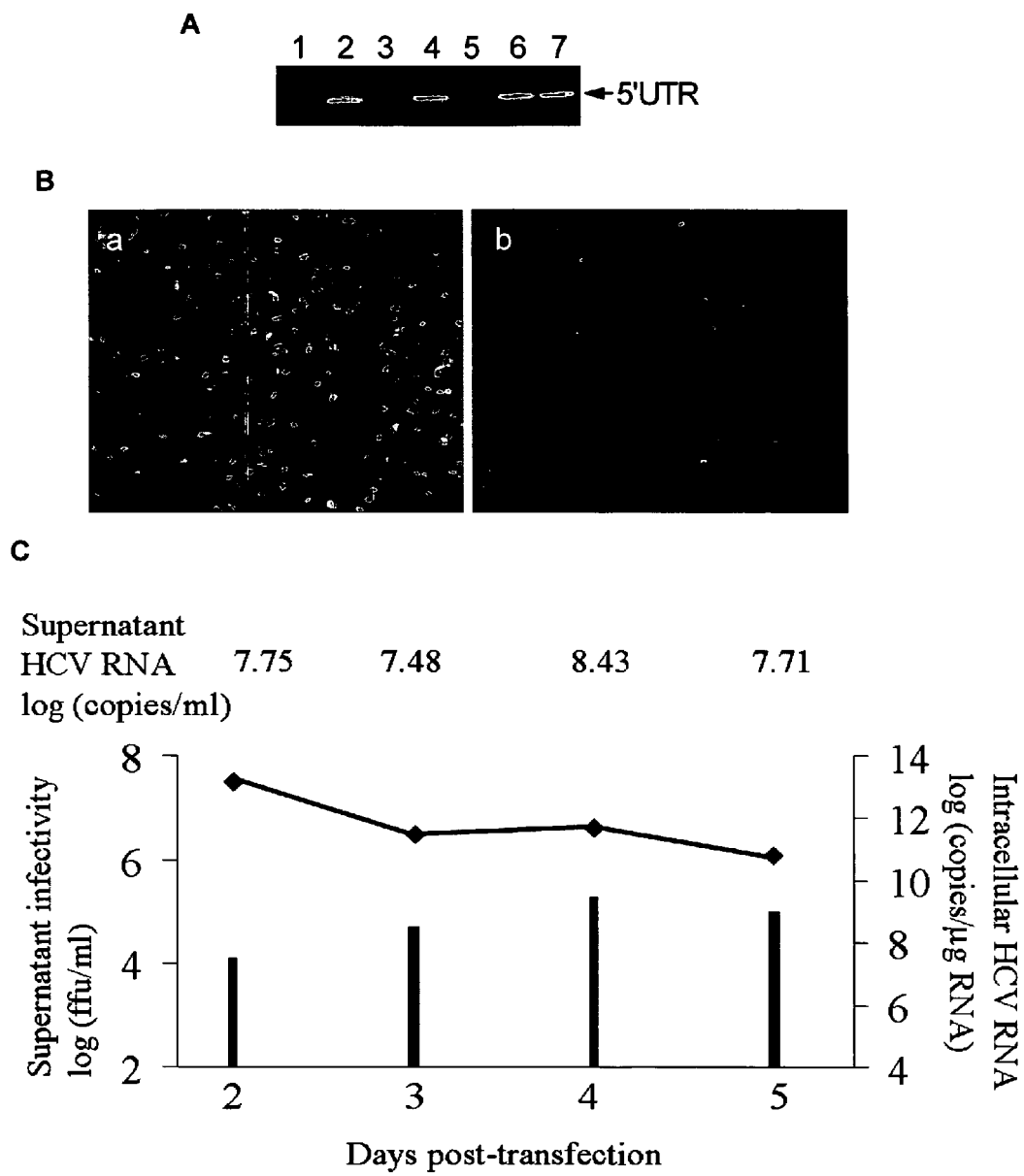
FIG. 4: Presence of HCV in culture medium and infectivity of naïve IHH. Panel A: RT-PCR analysis was performed for detection of 5' UTR from culture medium of HCV RNA transfected IHH. Filtered culture medium from IHH transfected with H77/GND RNA (lane 1), full-length H77 RNA (lane 2), JFH1/GND (lane 3), full-length JFH1 RNA (lane 4) were analyzed for amplification of 5' UTR. HCV genome was amplified similarly from Huh-7 cells transfected with JFH1/GND RNA (lane 5) and full-length JFH1 RNA (lane 6). Cloned H77 DNA was included as a positive control in PCR amplification (lane 7). Panel B: Immunofluorescence of IHH at day 3 after infection with filtered culture medium from H77 (panel a) and JFH1 (panel b) for detection of NS5a and NS3 protein expression, respectively. Panel C: Generation of infectious HCV after transfection of H77 genomic RNA into IHH. In vitro transcribed H77 RNA (2 ug) was electroporated into $1 \times 10^6$ IHH. HCV RNA copies at the intracellular (Δ-Δ) level and in the culture supernatant (numbers on top) were measured by real-time PCR at indicated days. Virus infectivity of the culture supernatant was determined in naive IHH and is expressed as ffu/ml (black bars). Panel D: Neutralization of virus infectivity by HCV infected patient serum (black bars). Two fold serial dilutions of test serum was incubated with ~100 fluorescent focus unit of virus generated from H77 clone at 37° C. for 30 minutes. Virus-serum mixture was added on naïve IHH and incubated for 3 days for determination of fluorescent focus unit by indirect immunofluorescence using NS5a specific antibody. Similar experiment was performed in parallel with serum from a healthy individual (hatched bars). The results are presented as % inhibition of fluorescent focus unit, and variation from triplicate assays are indicated by error bars.
Figure 4:
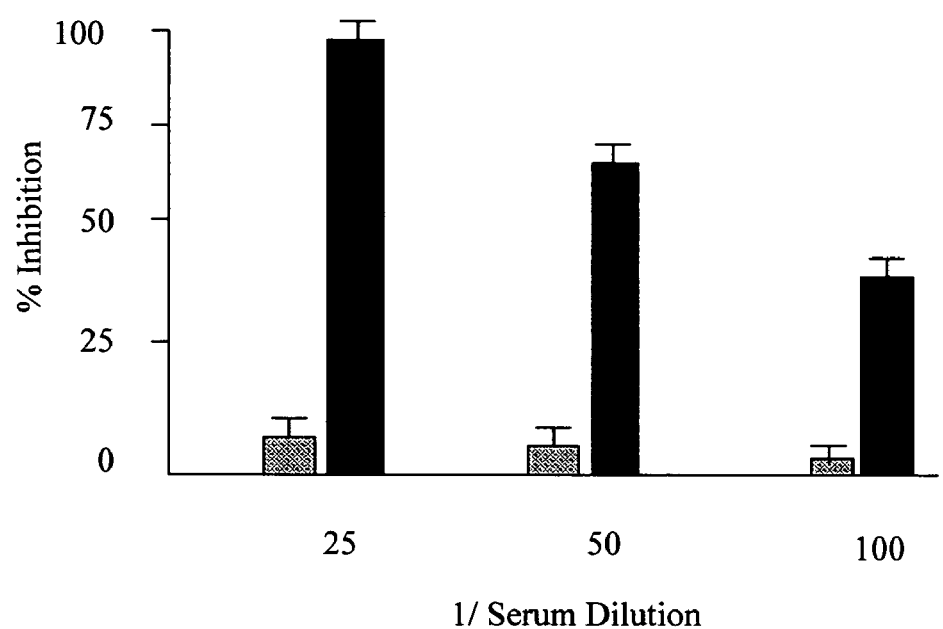

Inventors next examined the presence of HCV in cell culture medium from IHH. After different transfection time periods, culture medium was filtered through a 0.45 μm cellulose acetate membrane (Millipore, Bedford, Mass.), and concentrated to ~10-20 fold by Millipore ultrafiltration (100 kDa cut off) and used for detection of HCV genomic sequence by RT-PCR (FIG. 4, panel A). The presence of HCV 5' UTR was detected in culture medium from HCV genome transfected IHH, but not from polymerase defective HCV RNA transfected IHH. The inventors obtained ~$1.1 \times 10^8$ genome copies/ml of culture medium using real-time RT-PCR, as recently described (32). Culture supernatant collected for 7 days suggested a peak of HCV genome copy number between 4 and 5 days after transfection.

The inventors then determined whether the culture medium contained infectious HCV. For this, culture medium was serially diluted two fold and inoculated into naive IHH. Cells were incubated for 4 h, washed and incubated with fresh medium for 3 days before analysis of ffu/ml by indirect immunofluorescence for NS5a (H77 clone) or NS3 (JFH1 clone) as recently described (32). Nuclear staining was performed using TO-PRO3-iodide (Molecular Probes) and cells were mounted for confocal laser scanning microscopy (Bio-Rad, Model 1024). A representative figure displaying infection of IHH by H77 or JFH1 is shown (FIG. 4, panel B). The number of fluorescing cells was counted and correlated with dilutions of cell culture medium for determination of ffu/ml. The inventors observed a ~$4.5 \times 10^4$–$1 \times 10^5$ ffu/ml of the cell culture medium after 5 days of transfection from both H77 and JFH1 clones.

The inventors transfected in vitro transcribed H77 or JFH1 RNA into IHH and isolated RNA from transfected cells. Culture supernatant was also collected for isolation of RNA and determination of infectivity (ffu/ml). Real-Time PCR suggested maximal HCV RNA accumulation from H77 at the intracellular level on day 2, which declined on day 5 (FIG. 4, panel C). The inventors have observed higher genome copy number and infectious virus titer at day 4. Similarly, JFH1 RNA transfected IHH supernatant displayed a peak genome copy number of $10^8$/ml, and infectivity of ~$7 \times 10^4$ ffu/ml on day 4.

A HCV infected patient serum (OP1843) displaying neutralizing activity against VSV/HCV pseudotype (19) was used in determining neutralization of cell culture grown HCV. Serum from a healthy volunteer was used as a negative control in HCV neutralization assay. A two fold serial dilution of heat inactivated serum was incubated with ~100 fluorescent focus units of HCV generated from H77 clone at 37° C. for 30 minutes. Virus-serum mixture was added to naive IHH cultures and incubated for 3 days. Neutralization of fluorescent focus unit was determined from the inhibition of NS5a protein expression by immunofluorescence. Results are shown as percent inhibition of fluorescent focus unit (FIG. 4, panel D). A ~60% infectivity was inhibited upon prior incubation of HCV in culture medium with the patient serum at 1/50 dilution. Similar inhibition at different dilutions with three other HCV infected patient sera was also observed. In contrast, sera from 4 healthy individuals did not inhibit infectivity at 1/10 dilution. These results suggested that infectious HCV particles released in the culture medium are neutralized by specific antibodies.

REFERENCES

Applicants make no statement, inferred or direct, regarding the status of the following references as prior art. Applicants reserve the right to challenge the veracity of any statements made in these references, which are incorporated herein by reference.

1. Basu, A., K. Meyer, R. B. Ray, and R. Ray. 2001. Hepatitis C virus core protein modulates the interferon-induced transacting factors of JAK/Stat signaling pathway but does not affect the activation of IRF-1 or 561 genes. Virology 288:379-390.

2. Basu, A., K. Meyer, R. B. Ray, and R. Ray. 2002. Hepatitis C virus core protein is necessary for the maintenance of immortalized human hepatocytes. Virology 298:53-62.

3. Blight, K. J., J. A. McKeating, J. Marcotrigiano, and C. M. Rice. 2003. Efficient replication of hepatitis C virus genotype 1a RNAs in cell culture. J. Virol. 77:3181-3190.

4. Bode, J. G., S. Ludwig, C. Ehrhardt, U. Albrecht, A. Erhardt, F. Schaper, P. C. Heinrich, and D. Haussinger. 2003. IFN-alpha antagonistic activity of HCV core protein involves induction of suppressor of cytokine signaling-3. FASEB J. 17:488-490.

5. Cai, Z., C. Zhang, K. S. Chang, J. Jiang, B. C. Ahn, T. Wakita, T. J. Liang, and G. Lou. 2005. Robust production of infectious hepatitis C virus (HCV) from stably HCV cDNA-transfected human hepatoma cells. J. Virol. 79:13963-13973.

6. Di Bisceglie, A. M., R. L. Carithers, and G. J. Gores. 1998. Hepatocellular carcinoma. Hepatology 28:1161-1165.

7. Hayashi, J., H. Aoki, Y. Arakawa, and O. Hino. 1999. Hepatitis C virus and hepatocarcinogenesis. Intervirology 42:205-210.

8. Heller, T., S. Saito, J. Auerbach, T. Williams, T. R. Moreen, A. Jazwinski, B. Cruz, N. Jeurkar, R. Sapp, G. Luo, and T. J. Liang. 2005. An in vitro model of hepatitis C virion production. Proc. Natl. Acad. Sci. USA 102:2579-2583.

9. Hoofnagle, J. H., and A. M. Di Bisceglie. 1997. The treatment of chronic viral hepatitis. N. Eng. J. Med. 336:347-356.

10. Ikeda, M., M. Yi, K. Li, and S. M. Lemon. 2002. Selectable subgenomic and genome-length dicistronic RNAs derived from an infectious molecular clone of the HCV-N strain of hepatitis C virus replicate efficiently in cultured Huh-7 cells. J. Virol. 76:2997-3006.

11. Jeffers, L. 2000. Hepatocellular carcinoma: an emerging problem with hepatitis C. J. Natl. Med. Assoc. 92:369-371.

12. Kato, T., A. Furusaka, M. Miyamoto, T. Date, K. Yasui, J. Hiramoto, K. Nagayama, T. Tanaka, and T. Wakita. 2001. Sequence analysis of hepatitis C virus isolated from a fulminant hepatitis patient. J. Med. Virol. 64:334-339.

13. Kolykhalov, A. A., E. V. Agapov, K. J. Blight, K. Mihalik, S. M. Feinstone, and C. M. Rice. 1997. Transmission of hepatitis C by intrahepatic inoculation with transcribed RNA. Science 277:570-574.

14. Kolykhalov, A. A., K. Mihalik, S. M. Feinstone, and C. M. Rice. 2000. Hepatitis C virus-encoded enzymatic activities and conserved RNA elements in the 3' nontranslated region are essential for virus replication in vivo. J. Virol. 74:2046-2051.

15. Lindenbach, B. D., M. J. Evans, A. J. Syder, B. Wolk, T. L. Tellinghuisen, C. C. Liu, T. Maruyama, R. O. Hynes, D. R. Burton, J. A. McKeating, and C. M. Rice. 2005. Complete replication of hepatitis C virus in cell culture. Science 309:623-626.

16. Lin, W., W. H. Choe, Y. Hiasa, Y. Kamegaya, J. T. Blackard, E. V. Schmidt, and R. T. Chung. 2005. Hepatitis C virus expression suppresses interferon signaling by degrading STAT1. Gastroenterology 128:1034-1041.

17. Majumder, M., A. K. Ghosh, R. Steele, X. Y. Zhou, N. J. Phillips, R. Ray, and R. B. Ray. 2002. Hepatitis C virus NS5A protein impairs TNF-mediated hepatic apoptosis, but not by an anti-FAS antibody, in transgenic mice. Virology 294:94-105.

18. Melen, K., R. Fagerlund, M. Nyqvist, P. Keskinen, and I. Julkunen. 2004. Expression of hepatitis C virus core protein inhibits interferon-induced nuclear import of STATs. J. Med. Virol. 73:536-547.

19. Meyer, K., A. Beyene, T. L. Bowlin, A. Basu, and R. Ray. 2004. Coexpression of hepatitis C virus E1 and E2 chimeric envelope glycoproteins displays separable ligand sensitivity and increases pseudotype infectious titer. J. Virol. 78:12838-12847.

20. Miller, K., S. McArdle, M. J. Gale Jr, D. A. Geller, B. Tenoever, J. Hiscott, D. R. Gretch, and S. J. Polyak. 2004. Effects of the hepatitis C virus core protein on innate cellular defense pathways. J. Interferon Cytokine Res. 24:391-402.

21. Moradpour, D., and H. E. Blum. 1999. Current and evolving therapies for hepatitis C. Eur. J. Gastroenterol. Hepatol. 11:1199-1202.

22. Pawlotsky, J. M. 2005. Current and future concepts in hepatitis C therapy. Semin. Liver Dis. 25:72-83.

23. Pietschmann, T., V. Lohmann, A. Kaul, N. Krieger, G. Rinck, G. Rutter, D. Strand, and R. Bartenschlager. 2002. Persistent and transient replication of full-length hepatitis C virus genomes in cell culture. J. Virol. 76:4008-4021.

24. Prince A. M., T. Huima-Byron, T. S. Parker, and D. M. Levine. 1996. Visualization of hepatitis C virions and putative defective interfering particles isolated from low-density lipoproteins. J. Viral Hepat. 3:11-17.

25. Ray, R. B., K. Meyer, and R. Ray. 2000. Hepatitis C virus core protein promotes immortalization of primary human hepatocytes. Virology 271:197-204.

26. Ray, R. B., and Ray, R. 2001. Hepatitis C virus core protein: intriguing properties and functional relevance. FEMS Microbiol Lett. 202:149-156.

27. Saito, I., T. Miyamura, A. Ohbayashi, H. Harada, T. Katayama, S. Kikuchi, Y. Watanabe, S. Koi, M. Onji, Y. Ohta, Q. Choo, M. Houghton, and G. Kuo. 1990. Hepatitis C virus infection is associated with the development of hepatocellular carcinoma. Proc. Natl. Acad. Sci. USA 87:6547-6549.

28. Simmonds, P., E. C. Holmes, T. A. Cha, S. W. Chan, F. McOmish, B. Irvine, E. Beall, P. L. Yap, J. Kolberg, and M. S. Urdea. 1993. Classification of hepatitis C virus into six major genotypes and a series of subtypes by phylogenetic analysis of the NS-5 region. J. Gen. Virol. 74:2391-2399.

29. Wakita, T., T. Pietschmann, T. Kato, T. Date, M. Miyamoto, Z. Zhao, K. Murthy, A. Habermann, H. G. Krausslich, M. Mizokami, R. Bartenschlager, and T. J. Liang. 2005. Production of infectious hepatitis C virus in tissue culture from a cloned viral genome. Nature Med. 11:791-796.

30. Yanagi, M., R. H. Purcell, S. U. Emerson, and J. Bukh. 1997. Transcripts from a single full-length cDNA clone of hepatitis C virus are infectious when directly transfected into the liver of a chimpanzee. Proc. Natl. Acad. Sci. USA 94:8738-8743.

31. Zein, N. N., J. Rakela, E. L. Krawitt, K. R. Reddy, T. Tominaga, and D. H. Persing. Collaborative Study Group. 1996. Hepatitis C virus genotypes in the United States: epidemiology, pathogenecity, and response to interferon therapy. Ann. Intern. Med. 124:634-639.

32. Zhong, J., P. Gastaminza, G. Cheng, S. Kapadia, T. Kato, D. R. Burton, S. F. Wieland, S. L. Uprichard, T. Wakita, and F. V. Chisari. 2005. Robust hepatitis C virus infection in vitro. Proc. Natl. Acad. Sci. USA 102:9294-9299.

What is claimed is:

1. A cultured cell comprising, a) a human hepatocyte comprising HCV 1a cDNA, b) whereby the HCV 1a cDNA consists of HCV 1a cDNA encoding the HCV 1a core protein, c) whereby the cell is immortal, d) further comprising a full length hepatitis C virus 1a genome, e) whereby the full length hepatitis C virus 1a genome consists of RNA, f) whereby the cell is permissive for replication of the RNA genome and generation of infective hepatitis C virus 1a virus particles.

2. A cell derived from the cultured cell of claim 1, whereby the derived cell is permissive for replication of the RNA genome, and generation of infective hepatitis C virus 1a virus particles.

3. The derived cell of claim 2, whereby the derived cell is a product of cell fusion.

4. The derived cell of claim 2, whereby the derived cell is a product of genetic modification.

5. The cultured cell as in claim 1 wherein the full length hepatitis C virus 1a genome, consisting of RNA, is transcribed from the sequence set forth in SEQ ID NO:1.

6. The cultured cell as in claim 1 wherein the full length hepatitis C virus 1a viral RNA genome comprises at least 99 percent homology with RNA transcribed from the sequence set forth in SEQ ID NO:1.

7. The cultured cell as in claim 1 wherein the full length hepatitis C virus 1a viral RNA genome comprises at least 99 percent identical with RNA transcribed from the sequence set forth in SEQ ID NO:1.

* * * * *